(12) United States Patent
Hestad et al.

(10) Patent No.: US 7,922,745 B2
(45) Date of Patent: Apr. 12, 2011

(54) POSTERIOR DYNAMIC STABILIZATION OF THE SPINE

(75) Inventors: Hugh D. Hestad, Edina, MN (US); Mike E. Lancial, St. Louis Park, MN (US); John F. Otte, St. Anthony, MN (US); Scott C. Lynch, Plymouth, MN (US); John J. Grabowski, Bloomington, MN (US); Julie Osterberg, Waconia, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 1495 days.

(21) Appl. No.: 11/328,393

(22) Filed: Jan. 9, 2006

(65) Prior Publication Data

US 2007/0173818 A1 Jul. 26, 2007

(51) Int. Cl.
*A61B 17/70* (2006.01)
(52) U.S. Cl. ........................................................ 606/249
(58) Field of Classification Search .......... 606/246–249; 623/17.11–17.16
See application file for complete search history.

(56) References Cited

U.S. PATENT DOCUMENTS

| | | | |
|---|---|---|---|
| 5,496,318 A | 3/1996 | Howland et al. | |
| 5,645,599 A | 7/1997 | Samani | |
| 5,725,582 A | 3/1998 | Bevan et al. | |
| 5,836,948 A | 11/1998 | Zucherman et al. | |
| RE36,221 E | 6/1999 | Breard et al. | |
| 6,048,342 A | 4/2000 | Zucherman et al. | |
| 6,235,030 B1 | 5/2001 | Zucherman et al. | |
| 6,248,106 B1 | 6/2001 | Ferree | |
| 6,419,676 B1 | 7/2002 | Zucherman et al. | |
| 6,440,169 B1 | 8/2002 | Elberg et al. | |
| 6,451,019 B1 | 9/2002 | Zucherman et al. | |
| 6,461,359 B1 | 10/2002 | Tribus et al. | |
| 6,582,433 B2 | 6/2003 | Yun | |
| 6,699,247 B2 * | 3/2004 | Zucherman et al. | 606/86 A |
| 6,743,257 B2 | 6/2004 | Castro | |
| 2002/0095154 A1 * | 7/2002 | Atkinson et al. | 606/61 |
| 2003/0220643 A1 * | 11/2003 | Ferree | 606/61 |
| 2004/0006343 A1 * | 1/2004 | Sevrain | 606/61 |
| 2004/0243239 A1 | 12/2004 | Taylor | |

FOREIGN PATENT DOCUMENTS

NL 7610576 3/1978

OTHER PUBLICATIONS

International Search Report and Written Opinion, Aug. 15, 2007, 8 pgs.

* cited by examiner

*Primary Examiner* — Eduardo C Robert
*Assistant Examiner* — Mary Hoffman
(74) *Attorney, Agent, or Firm* — Seager, Tufte & Wickhem, LLC

(57) ABSTRACT

An interspinous vertebral implant comprises a resiliently compressible body that is adapted for position between adjacent superior and inferior spinous processes, and an anchoring member that is affixed to the superior and the inferior spinous processes posterior to the resiliently compressible body. The anchoring member provides a compressive force while the resiliently compressible body provides a distraction. Without being bound by any theory, it is believed that the combination of the distraction and compressive forces created by this type of interspinous vertebral implant results in a rotational moment, which alleviates compression on the intervertebral disk.

6 Claims, 9 Drawing Sheets

POSTERIOR DYNAMIC STABILIZATION OF THE SPINE

FIELD OF THE INVENTION

The present invention relates to interspinous vertebral implants and methods for using the same for dynamic stabilization of spine.

BACKGROUND OF THE INVENTION

Damage to an intervertebral disk typically results in abnormal play of the vertebrae contiguous to this disk. This play subjects the posterior articular processes to considerable stresses, generating very painful wear and tear of these processes and general instability of the spinal column. Such instability can also result from an operation performed on a herniated intervertebral disk, which entails access to the disk, thereby weakening the ligament system of the articulation, or can result from certain cases of arthrosis which also subjects the posterior articulations to considerable and painful stresses.

Early implant devices for bracing the spinal column comprise rigid elements which are connected to means of osseous anchoring. The rigid elements frequently consist of metal rods which are implanted along several vertebrae, on either side of the spinous processes. These early devices had the disadvantage of being difficult to implant, and necessitated considerable and complex work in putting them into place. Moreover, they immobilized a relatively long vertebral segment, which significantly reduced the mobility of the patient and subjected the articulations situated on either side of this rigid segment to considerable stresses which often generated new pathological conditions.

Some recently developed interspinous stabilizers are designed to be inserted between the spinous processes. For example, one such stabilizer comprises an interspinous bearing cushion which is fixed to the spinal column by a textile ligament which surrounds the processes. One of the major disadvantages of the bearing cushion is being relatively rigid and holding the vertebrae in a specific position, thereby creating discomfort for the patient. In addition, the bearing cushion tends to wear under the influence of repeated stresses to which it is subjected.

Other relatively recent interspinous stabilizers have anchoring members, which are adapted to be attached to processes, directly perpendicular to a spring body that provides stability during extension. These interspinous stabilizers, while helpful in limiting the range of spinal motion during extension, lack sufficient support in flexion and thus may create a flat back or kyphotic positioning in the spine. Moreover, these interspinous stabilizers may produce an undesirable load environment at adjacent spine levels.

Therefore, there is a need for interspinous stabilizers that can provide stability during both flexion and extension.

SUMMARY OF THE INVENTION

One aspect of the present invention provides methods and devices for dynamically stabilizing adjacent vertebral bodies. In one embodiment, methods of the present invention include inserting a resiliently compressible body between adjacent superior and inferior spinous processes, where the resiliently compressible body contacts the respective surfaces of the spinous processes thereby providing a distraction between the superior and inferior spinous processes and affixing an anchoring member to the superior and inferior spinous processes relatively posterior to the resiliently compressible body thereby providing a rotational moment which reduces the amount of compressive force in the anterior portion of the vertebral body.

One aspect of the present invention provides an interspinous vertebral implant that includes a distracting member comprising a compressible body adapted for positioning between adjacent superior and inferior spinous processes and an anchoring member that is capable of applying compressive force, wherein said anchoring member is capable of being anchored to the superior spinous process and the inferior spinous process.

In one embodiment, the interspinous stabilizer of the present invention comprises a resiliently compressible body that is adapted to be inserted between adjacent superior and inferior spinous processes. In this manner, the resiliently compressible body contacts the respective surfaces of the spinous processes thereby providing a distraction between the superior and inferior spinous processes. The interspinous stabilizers also comprise an anchoring member that can be used to affix the stabilizers to the superior and inferior spinous processes relatively posterior to the resiliently compressible body. Typically, the anchoring member also provides a compressive force to the spinous processes. Without being bound by any theory, it is believed that the combination of the distraction and compressive forces results in creation of a rotational moment that is believed to reduce the amount of compressive force in the anterior portion of the vertebral body, in particular on the intervertebral disk. Thus unlike other conventional interspinous stabilizers, it is believed that the interspinous stabilizers of the present invention reduce the amount of compressive force on the intervertebral disk thereby providing a significant relief to a patient.

DETAILED DESCRIPTION OF THE INVENTION

General Overview

Figure 1A:
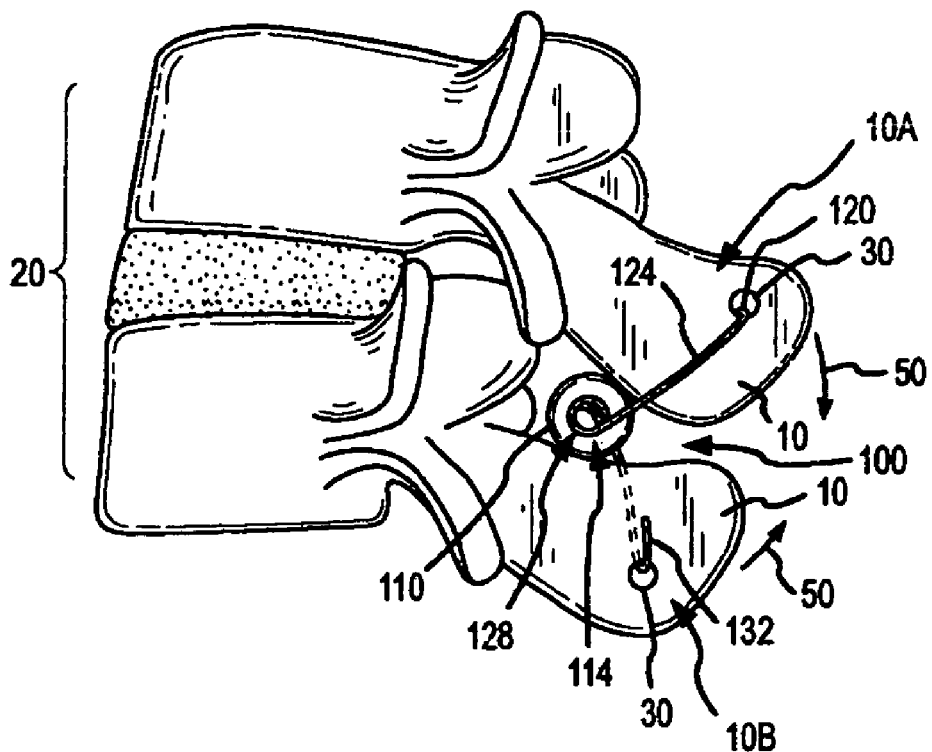
FIG. 1A is a side view of one embodiment of the interspinous stabilizer of the present invention following implantation.

The present invention provides implantable interspinous stabilizers that provide a dynamic stability during flexion and extension and methods for using the same. In particular, the present invention provides methods and interspinous stabilizers that provide a distraction force between the adjacent superior and inferior spinous processes and a posterior compressive force on these spinous processes. As used herein, "compressive force" refers to a force that, in the absence of any counter force, will cause two spinous processes to move closer to one another. And the terms "distraction" or "distraction force" refers to a force that, in the absence of any counter force, will cause two vertebral bodies to move further apart from one another. Distraction of the adjacent spinous processes is provided by placing a distraction member between the adjacent superior and inferior spinous processes. Typically, the distraction member comprises a resiliently compressible body that can be deformed when compressed. The term "resilient" has the conventional meaning known to one skilled in the art, including having a characteristic of being capable of withstanding a substantial amount of external force without being permanently deformed and being able to revert back to substantially its original shape when the external force is removed.

The interspinous stabilizers and methods of the present invention prevent or reduce the incidence of a flat back or kyphotic positioning in the spine by providing, in addition to distraction, a compressive force on the adjacent spinous processes, thereby at least partially counteracting the effect of distraction. Such a compressive force is generally applied using at least one anchoring element that is affixed to the spinous processes. The anchoring element is typically affixed relatively posterior to the location of the distractive member.

The anchoring element is adapted to exert a compressive force on the superior spinous process and the inferior spinous process that, in the absence of any counter force, will result in bringing these two spinous processes closer to each other. Combination of the distraction member and the compressive force results in a rotational moment of vertebrae with the distraction element being the center of the rotational moment. As used herein, "rotational moment" refers to the force that is exerted to the adjacent vertebrae such that a compressive force is exerted on the spinous processes of the two vertebrae and a separation force is exerted on the anterior portion of the two vertebrae, e.g., vertebral bodies. That is, the term refers to restoring lordosis, i.e., force restoring the normal curvature of the spine. Without being bound by any theory, it is believed that this rotational moment exerts a separation force that, in the absence of any counter force, will cause the anterior portion of the two vertebral bodies to move further apart (or at least reduce the amount of compressive force) from one another thereby providing at least a partial relief from compression of the intervertebral disk, especially on the anterior portion of the intervertebral disk.

The distraction element is adapted to be placed between adjacent superior and inferior spinous processes and contacting the respective surfaces of the spinous processes. Once implanted, the distraction element stabilizes and provides additional support during extension of the spine. During flexion, the compressive force of the anchoring element increases as the amount of flexion increases, thereby providing proportionally increasing counter force to the amount of flexion. Accordingly, interspinous stabilizers of the present invention provide a dynamic stability during both flexion and extension.

Interspinous Stabilizers

The present invention will now be described with regard to the accompanying drawings which assist in illustrating various features of the invention. In this regard, the present invention generally relates to interspinous stabilizers and methods for using the same. That is, the invention relates to implants that are intended to be inserted between the spinous processes of two contiguous vertebrae.

Several different embodiments of the present invention interspinous stabilizers are generally illustrated in the accompanying FIG. 1A through 9C, which are provided for the purpose of merely illustrating the practice of the present invention. It should be appreciated that these Figures are presented only for illustrative purposes and do not constitute limitations on the scope of the present invention.

Figure 1B:
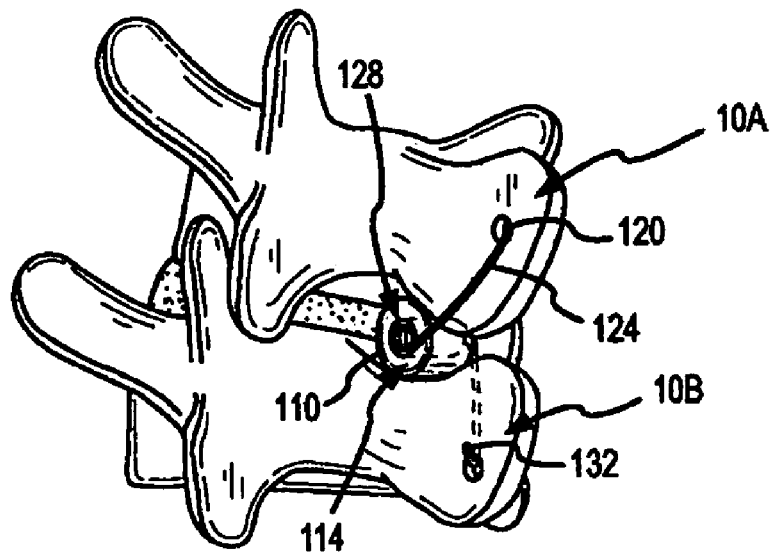
FIG. 1B is a perspective view of FIG. 1A.

Referring now to FIG. 1A and 1B, in one particular embodiment of the present invention the interspinous stabilizer 100 comprises a distraction element 110 and an anchoring element 120. As can be seen, the anchoring element 120 is attached to the spinous process 10 of two adjacent vertebrae 20 near the posterior end of the spinous processes 10. The two arms 124 of the anchoring element 120 extend anteriorly and posteriorly to engage the spinous processes 10A and 10B. The two anchoring element arms 124 are joined by a spring configuration 128. In FIG. 1A and 1B, the spring portion 128 that is connected to the anchoring element arms 124 is a coil spring configuration; however, it should be appreciated that other spring configurations known to one skilled in the art can also be used. The coil spring 128 is at least partially enclosed or encapsulated within a resiliently compressible body 114 to form the distraction element 110. The overall shape of the distraction element 110 is not critical as long as it can be inserted between two adjacent spinous processes 10 to provide a sufficient distraction necessary to stabilize the spine. For example, the overall shape of the distraction element 110 can be rectangular, oblong, oval, etc. Typically, however, the overall shape of the distraction element 110 in FIGS. 1A and 1B is cylindrical.

The resiliently compressible body 114 can be made from any suitable material known to one skilled in the art including, but not limited to, elastomer, plastic, rubber, silicon, or a combination thereof Typically, the resiliently compressible body is made from a material comprising an elastomeric material. It should be appreciated, however, that regardless of the material used, the outer surface of the resiliently compressible body 114 is preferably biocompatible or non-immunogenic. While not shown in any of the drawings, the resiliently compressible body 114 can alternatively comprise a spring that is at least partially enclosed or encapsulated within a non-elastomeric or an elastomeric material. In this manner, the majority of resiliency is attributable to the spring rather than the material itself The force of the anchoring element arms 124 is applied to the spinous processes 10 posterior to the center of the coil spring 128 and the resiliently compressible body 114. The interspinous stabilizer 100 is shown in FIG. 1A and 1B with the anchoring element 120 attached to the spinous processes 10 through a hole 30 in the spinous processes. In this particular embodiment, the anchoring element 120 comprises two anchoring element arms 124 each of which goes through the each of the respective holes 30 in the spinous processes 10 and hooks to the other side of the spinous processes 10. However, it should be appreciated that a variety of other methods, such as a screw or nuts and bolts, known to one skilled in the art can also be used to affix the anchoring element 120 to the spinous processes 10.

The distraction element 110, comprising coil spring 128 and the resiliently compressible body 114, provides distraction of the spinous processes 10 on the anterior portion while the anchoring element 120 through two arms 124 of the coil spring 128 is adapted to provide compressive forces (as illustrated by the arrows 50) on the posterior portion of the spinous processes 10. Without being bound by any theory, it is believed that the compressive force applied by the anchoring element 120 creates a lever or a rotational moment while maintaining lordosis of the spine section.

Figure 2A:
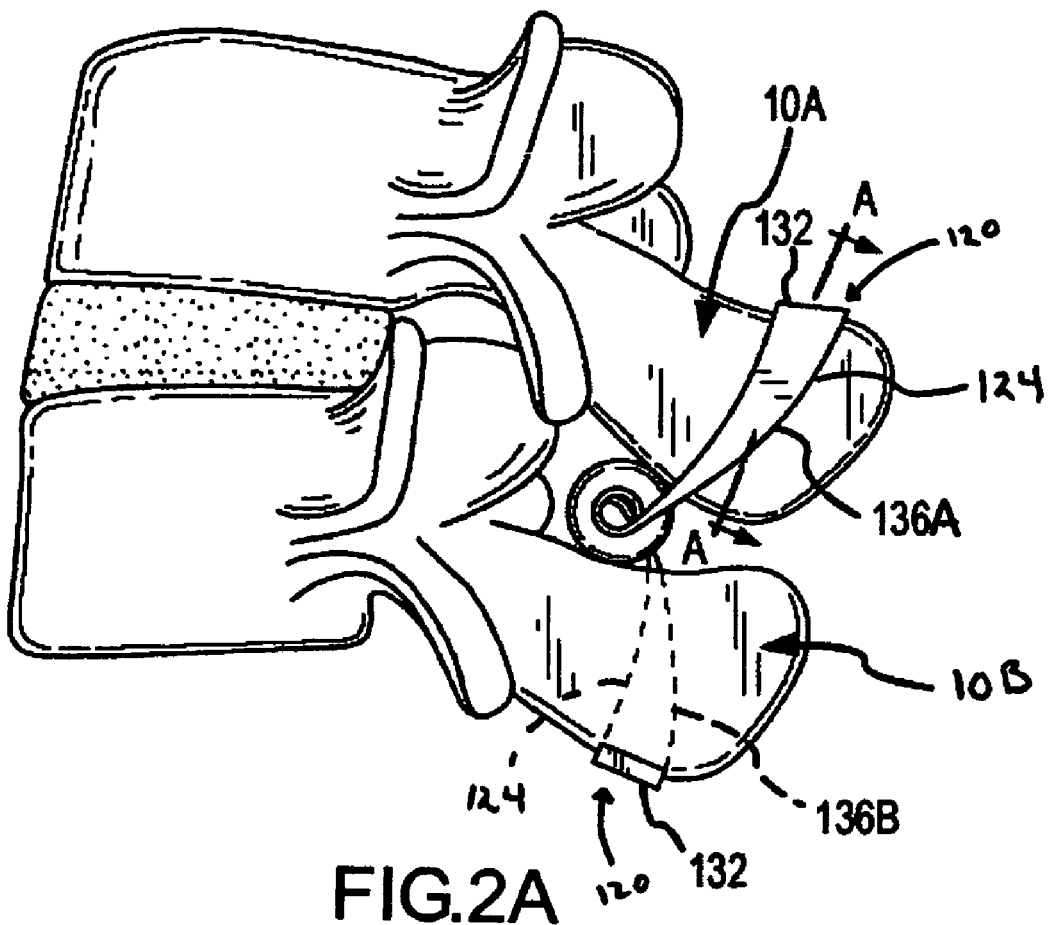
FIG. 2A is a side view of another embodiment of the interspinous stabilizer of the present invention following implantation.
Figure 2B:
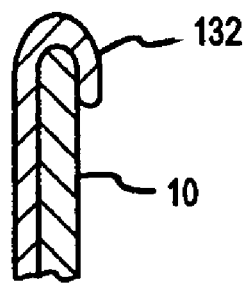
FIG. 2B is a plane view of FIG. 2A in the plane A-A showing a method of anchoring the interspinous stabilizer shown in FIG. 2A.

As stated above, a variety of other methods are known to one skilled in the art for affixing the anchoring element 120 to the spinous processes 10. FIGS. 2A and 2B illustrate one of the alternative methods for affixing the anchoring element 120 to the spinous processes 10. In this example, the anchoring element arms 124 are terminated with a U-shaped end 132. In affixing the anchoring element 120 to the spinous processes 10, the U-shaped end 132 is used to hook the anchoring element arms 124 onto the spinous processes 10. Once the U-shaped end 132 is hooked onto the edges of the spinous process 10, the U-shaped end 132, which maybe malleable, can be crimped to the bone to provide a tighter linkage. As shown in FIG. 2A, the width of the anchoring element arms 124 can be tapered such that the width of the anchoring element arm 124 near the U-shaped end 132 is wider than the width of the anchoring element arm near the distraction element 110.

Figure 3A:
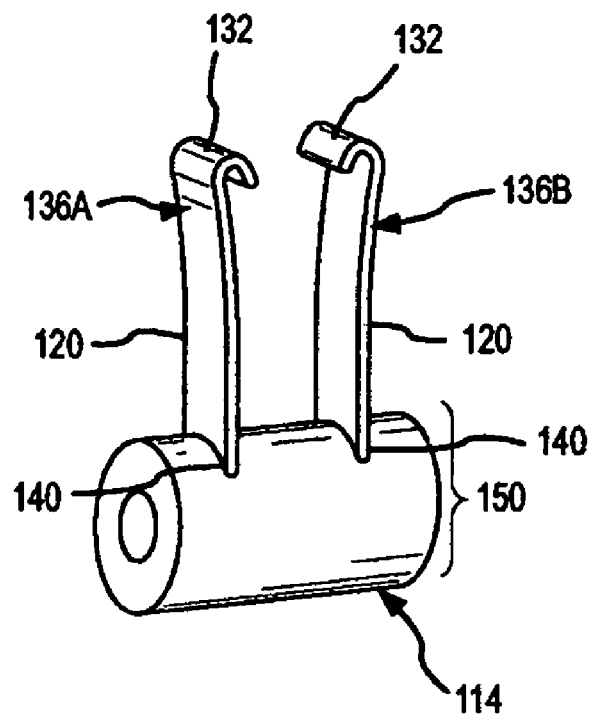
FIG. 3A is a perspective view of another embodiment of the interspinous stabilizer of the present invention.
Figure 3B:
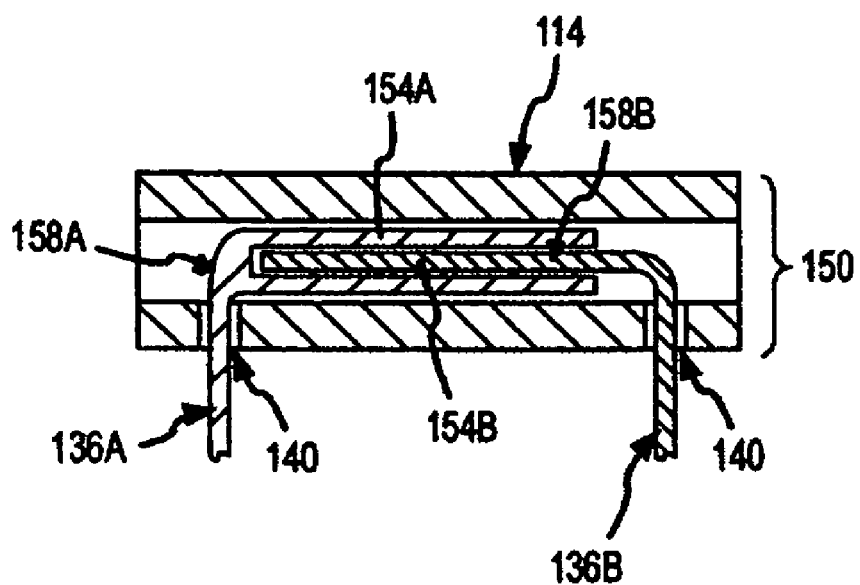
FIG. 3B is a cross-sectional view of the interspinous stabilizer of FIG. 3A.

FIGS. 3A and 3B illustrate another distraction element. In this illustration, the anchoring element 120 is similar to those described above in reference to FIGS. 2A and 2B; however, it should be appreciated that the U-shaped end 132 is not essential and other configurations of the anchoring element 120 can be used to affix the anchoring element 120 to the spinous processes 10. In FIGS. 3A and 3B, the distraction element comprises coupled body unit 150 that is encompassed or encapsulated within a resiliently compressible body 114. Typically, the resiliently compressible body 114 is made from a material comprising an elastomeric material. As stated above, the shape of the distraction element is not important as long as it is adapted to be placed between two adjacent spinous processes 10, i.e., a superior and an inferior spinous processes, 10A and 10B, respectively. Typically, however, the distraction element is cylindrical in shape.

The coupled body unit 150 comprises a first rigid piece 154A and a second rigid piece 154B. The first rigid piece 154A comprises a first coupling member 158A and a first anchoring member 136A. Similarly, the second rigid piece 154B comprises a second coupling member 158B and a second anchoring member 136B. Both of the first anchoring member 136A and the second anchoring member 136B are adapted to be affixed to the superior spinous processes 10, at a location posterior to the distraction element 110, e.g., the elastomeric body. As shown in FIG. 3B, when coupled together, the first coupling member 158A and the second coupling member 158B are adapted to rotate relative to each other.

The coupled body unit 150 can further comprise a spring or a spring-like mechanism (not shown) within its body such that when the first coupling member 158A and the second coupling member 158B are rotated relative to each other, the rotation creates a rotational moment that exerts a force to bring the first rigid piece 154A and the second rigid piece 154B to its resting position. The resting position of the first rigid piece 154A and the second rigid piece 154B, relative to each other, can be parallel, i.e., in the same plane and direction to one another as shown in FIG. 3A or be parallel but the direction of the first rigid piece 154A and the second rigid piece 154B can be at an angle relative to one another. The degree of angle between the first rigid piece 154A and the second rigid piece 154B can range anywhere between 0° (parallel and in the same direction) and 90°, preferably 0° and 60°. It should be appreciated, however, that any angle necessary to affix the first rigid piece 154A and the second rigid piece 154B to their respective spinous processes at a resting or "natural" position of the spinous processes maybe used.

It should be appreciated that any method or device known in the art of mechanical devices or one skilled in the art can be utilized for coupling the first rigid piece 154A and the second rigid piece 154B. Suitable coupling mechanisms include, but are not limited to, a socket and a socket insert, as illustrated in FIG. 3B, and a ball and socket coupling mechanism. While FIG. 3B shows the first coupling member 158A as a female part and the second coupling member 158B as a male part, this configuration can be switched.

In one illustrative example, a rotational moment is generated between the first rigid piece 154A and the second rigid piece 154B by using the elastomeric body (i.e., a resiliently compressible body 114) to generate a spring-like action. For example, in FIGS. 3A and 3B, the elastomeric body comprises two radial slots 140 through which the first anchoring member 136A and the second anchoring member 136B protrude. In FIG. 3A, the first rigid piece 154A and the second rigid piece 154B are parallel to one another in the same direction. When the first anchoring member 136A and the second anchoring member 136B are affixed to the superior spinous process 10A and the inferior spinous process 10B, respectively, (spinous processes are not shown in FIGS. 3A and 3B) the elastomeric body becomes twisted (not shown), thereby creating a spring-like action on the elastomeric body resulting in a generation of a rotational moment on the first rigid piece 154A and the second rigid piece 154B. In this case, the material used for the elastomeric body should be such that it is able to generate a sufficient rotational moment to be useful.

Figure 4A:
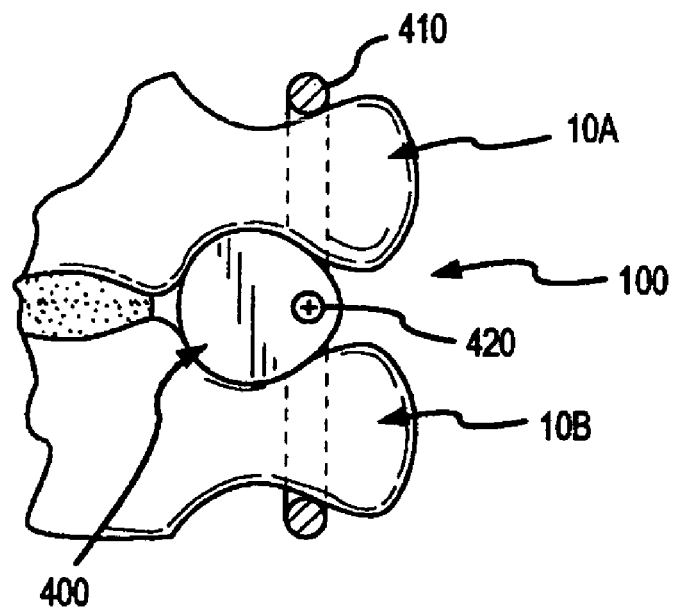
FIGS. 4A and 4B are side views of another embodiment of the interspinous stabilizer of the present invention with different anchoring member shapes.
Figure 4B:
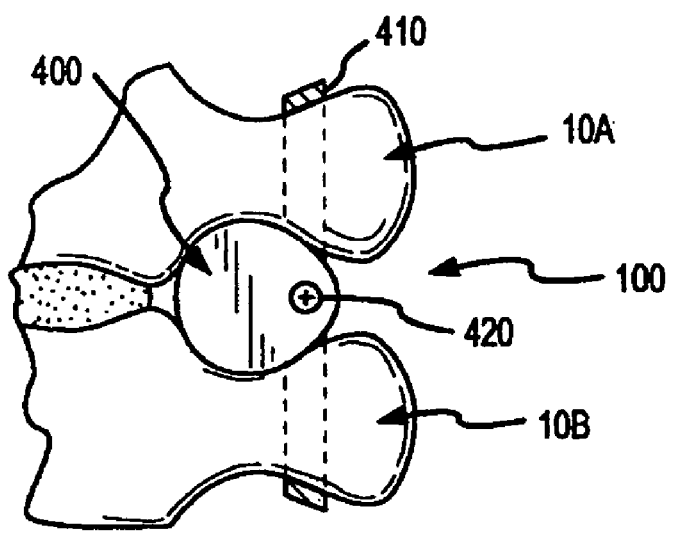

Another example of the interspinous stabilizer 100 of the present invention is exemplified in FIGS. 4A and 4B. In this example, the distraction element comprises a resiliently compressible tri-lobular shaped body 400 (i.e., triangular in shape with rounded edges thereby providing eccentric placement of arms). The anchoring element comprises a resiliently stretchable anchoring member 410. Preferably, the anchoring element is located posterior to the mid-point of body 400. When implanted, the resiliently stretchable anchoring member 410 is affixed or anchored to the spinous processes 10. As the figures illustrate, the resiliently stretchable anchoring member 410 is attached to a region that is posterior to the mid-point or the center of the tri-lobular shaped body 400. The interspinous stabilizer 100 of FIGS. 4A and 4B can be constructed as one piece unit, or it can be constructed as two or more piece unit in which a fastener or other fastening mechanism 420 is used to attach the resiliently stretchable anchoring member 410 to the resiliently compressible tri-lobular shaped body 400.

The interspinous stabilizer 100 of FIGS. 4A and 4B can also include a fixation member (not shown) to attach the interspinous stabilizer 100 to a pedicle (not shown). Suitable fixation members are well known to one skilled in the art and include, but are not limited to, a screw, a nut and bolt, or other mechanism suitable for affixing or attaching the resiliently compressible tri-lobular body 400 and/or the resiliently stretchable anchoring member 410 to the pedicle. This fixation member (not shown) can be used in place of or in addition to a fastener 420 to attach the anchoring member 410 to the resiliently compressible tri-lobular body 400 and/or the pedicle (not shown).

Figure 5:
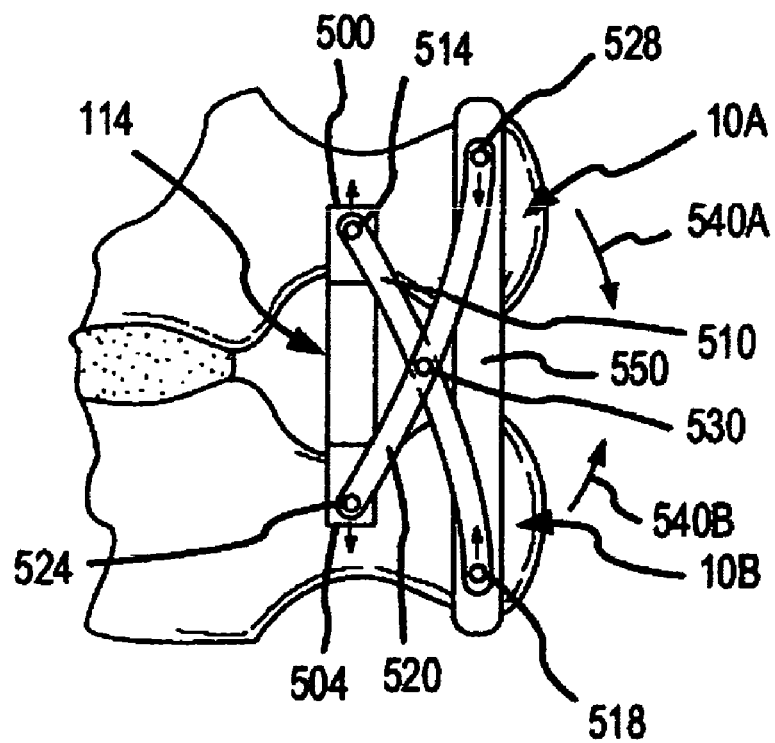
FIG. 5 is a side view of another embodiment of the interspinous stabilizer of the present invention following implantation.

FIG. 5 shows an interspinous stabilizer 100 having a resiliently compressible body 114 that comprises a top end 500 and a bottom end 504 that are adapted for contacting the surfaces of superior spinous process 10A and inferior spinous process 10B, respectively. The interspinous stabilizer 100 of FIG. 5 also comprises a first non-elastic anchoring member 510, a second non-elastic anchoring member 520, and a hinge 530 that operatively joins the first non-elastic anchoring member 510 and the second non-elastic anchoring member 520.

The first non-elastic anchoring member 510 comprises a first anterior anchoring end 514 that is connected to the top end 500 of the resiliently compressible body 114 and a first posterior anchoring end 518 that is adapted for anchoring or affixing to the inferior spinous process 10B posterior to the resiliently compressible body 114. The second non-elastic anchoring member 520 comprises a second anterior anchoring end 524 that is connected to the bottom end 504 of the resiliently compressible body 114 and a second posterior anchoring end 528 that is adapted for anchoring or affixing to the superior spinous process 10A posterior to the resiliently compressible body 114. The hinge 530 joins the two anchoring members 510 and 520 at a location between the anterior anchoring ends and the posterior anchoring ends such that the first and the second non-elastic anchoring members 510 and 520 form an X-shape like configuration. As can be seen in FIG. 5, a distraction force is supplied by a spacer (i.e., a resiliently compressible body 114) between the top end 500 and the bottom end 504. This results in a compressive force being applied at posterior portion of the spinous processes 10 as illustrated by arrows 540A and 540B.

Optionally, a tensile member 550 that is resiliently stretchable can also be provided, e.g., at or near the first and the second posterior anchoring ends 518 and 528. Without being bound by any theory, it is believed that the tensile member 550 can provide additional distraction between the top end 500 and the bottom end 504 and additional compressive force between the posterior portions of the spinouas processes 10. Additionally, a torsion spring (not shown) can also be placed at or near the hinge 530 resulting in a further distraction between the top end 500 and the bottom end 504 and compression between the first and the second posterior anchoring ends 518 and 528.

The first non-elastic anchoring member 510 and the second non-elastic anchoring member 520 can be affixed to the bone or simply wrapped around the spinous processes 10. Suitable methods for affixing anchoring members 510 and 520 are well known to one skilled in the art.

Figure 6:
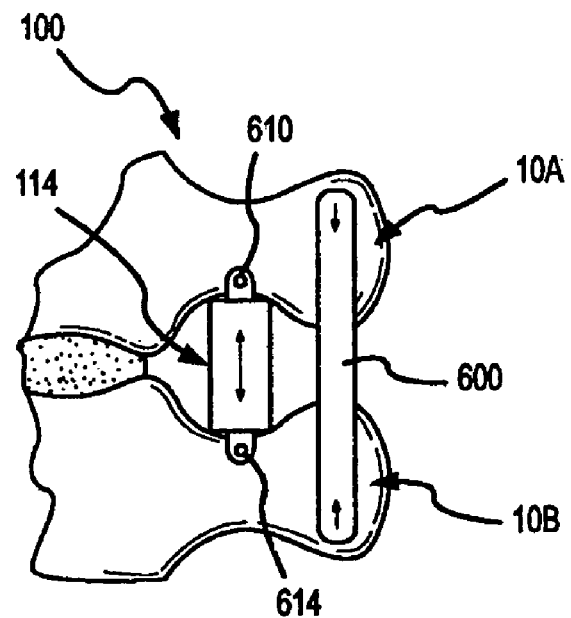
FIG. 6 is a side view of another embodiment of the interspinous stabilizer of the present invention following implantation.

The interspinous stabilizer 100 of the present invention can also be a two piece unit as illustrated in FIG. 6. The two piece unit comprises a resiliently compressible body 114 that serves as a distraction member and an operatively interconnected resiliently stretchable member 600 that is designed to create or generate a compressive force posterior to the distraction member. The distraction member (i.e., resiliently compressible body 114) and the resiliently stretchable member 600 are operatively interconnected by the virtue of having both of them being connected to the same adjacent spinous processes. The resiliently compressible body 114 comprises a top anchoring end 610 and a bottom anchoring end 614 for affixing the distraction member to the superior and inferior spinous processes 10A and 10B.

Similar to other illustrated devices, the interspinous stabilizer 100 shown in FIG. 6 comprises a compressive force generating piece (i.e., resiliently stretchable member 600) that is located posterior to the distraction member. It should be appreciated that the distraction member and the resiliently stretchable member 600 can be an integral unit. As with other interspinous stabilizers 100 described herein, either one or both of the distraction member and a compressive force generating member can be attached to the bone or can simply be wrapped around the superior surface of the superior process 10A or inferior surface of the inferior process 10B.

Figure 7:
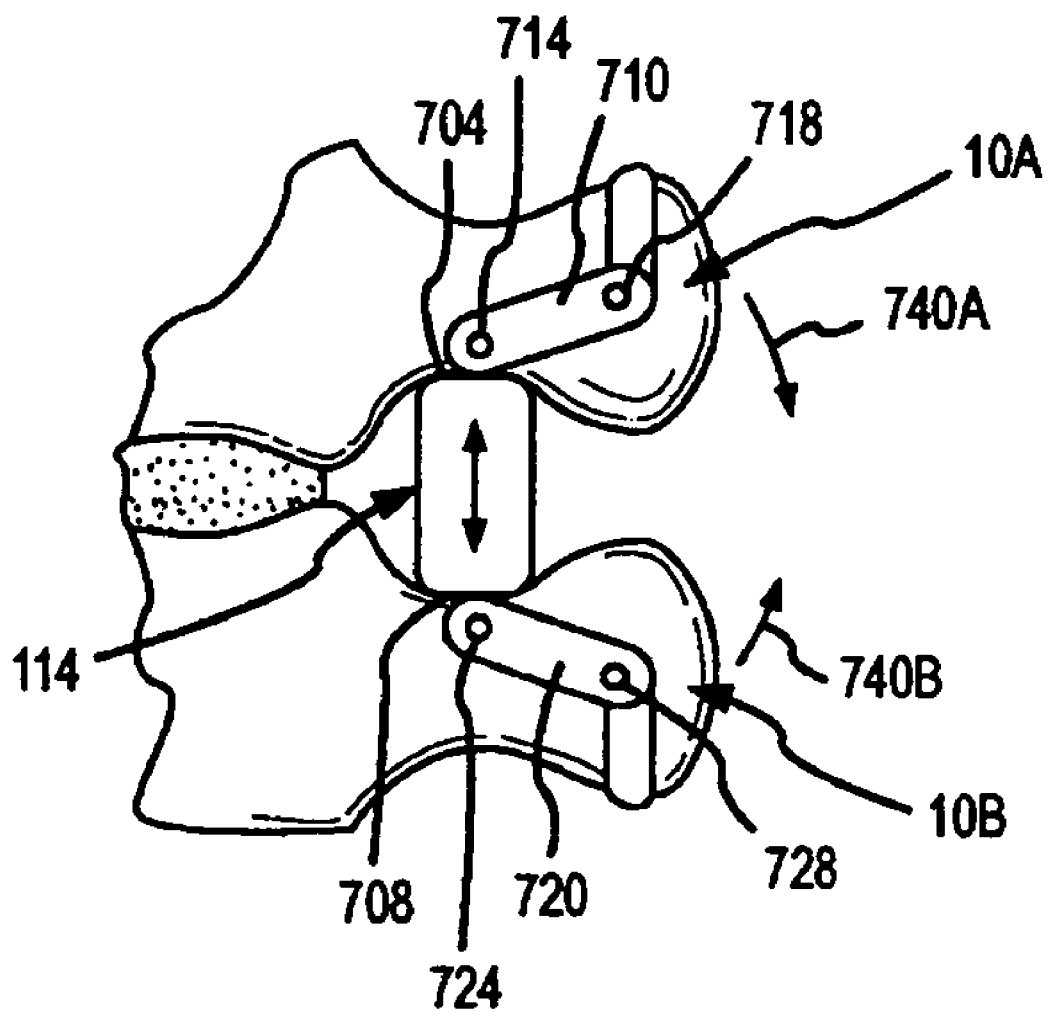
FIG. 7 is a side view of another embodiment of the interspinous stabilizer of the present invention following implantation.

FIG. 7 illustrates an interspinous stabilizer 100 of the present invention that comprises a resiliently compressible body 114 comprising a top end 704 and a bottom end 708. The interspinous stabilizer 100 of FIG. 7 further comprises a superior anchoring member 710 and an inferior anchoring member 720. The superior anchoring member 710 comprises a superior anterior anchoring end 714 that is connected to the top end 704 and a superior posterior anchoring end 718 that is adapted for anchoring to the superior spinous process 10A posterior to the resiliently compressible body 114. Likewise, the inferior anchoring member 720 comprises an inferior anterior anchoring end 724 that is connected to the bottom end 708 and an inferior posterior anchoring end 728 that is adapted for anchoring to the inferior spinous process 10B posterior to the resiliently compressible body 114.

As stated before, the resiliently compressible body 114 can include a coil spring (not shown) encapsulated within a body to provide resiliency. In this manner, the body 114 can comprise a non-resilient material. Referring again to FIG. 7, the resiliently compressible body 114 is placed between a superior spinous process 10A and an inferior spinous process 10B to create a desired distraction. A compressive force is applied to the spinous processes 10 posterior to the resiliently compressible body 114. Without being bound by a theory, it is believed that having both the compressive force and distraction results in creation of a rotational moment as indicated by arrows 740A and 740B. Implantation of the implantable stabilizer 100 of FIG. 7 is typically carried out by affixing the superior anchoring member 710 and the inferior anchoring member 720 to the spinous processes 10 while the rotational moment is applied.

Figure 8A:
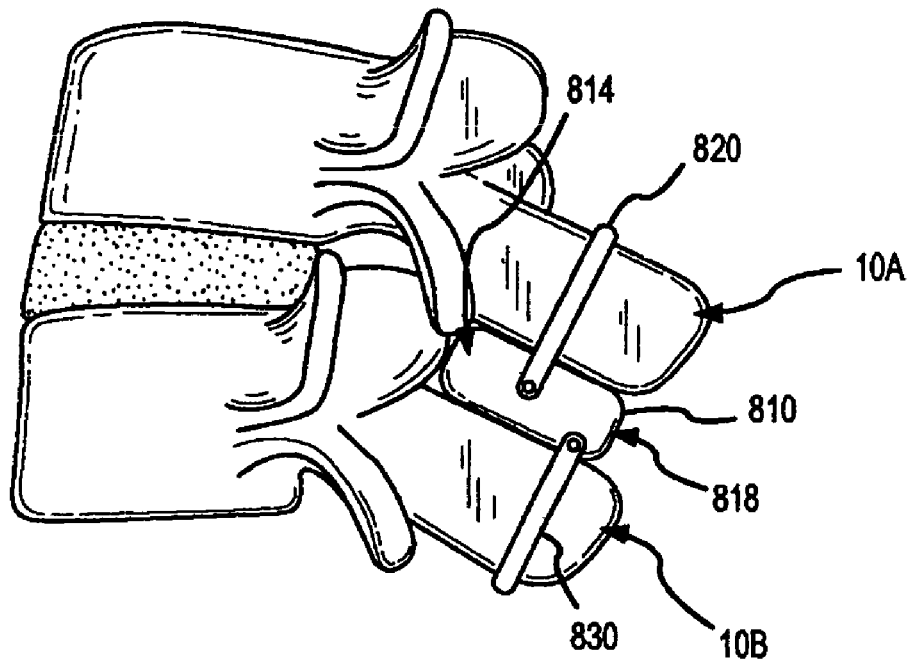
FIG. 8A is a side view of another embodiment of the interspinous stabilizer of the present invention following implantation and at resting stage.
Figure 8B:
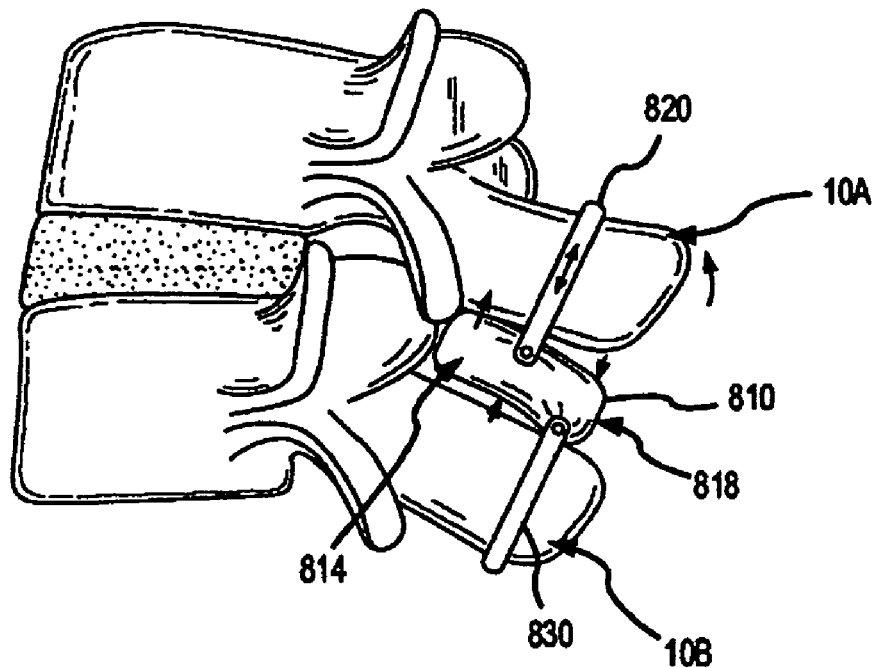
FIG. 8B is a side view of the interspinous stabilizer of FIG. 8A at flexion.

FIGS. 8A and 8B illustrate an interspinous implant that comprises a resiliently compressible elongated body 810, a first anchoring member 820 and a second anchoring member 830. The resiliently compressible elongated body 810 is adapted for positioning between a superior spinous process 10A and an inferior spinous process 10B. The resiliently compressible elongated body 810 comprises an anterior end 814 and a posterior end 818. Each of the anchoring members 820 and 830 is comprised of an elastic material, a rod, or other similar material, or a combination thereof. Typically, these anchoring members 820 and 830 serve as struts and each is comprised of a relatively stiff or non-stretchable material.

Referring again to FIGS. 8A and 8B, the first anchoring member 820 is affixed to the superior spinous process 10A while the second anchoring member 830 is affixed to the inferior spinous process 10B. In addition, two anchoring members 820 and 830 are attached to the resiliently compressible elongated body 810 at different positions of the resiliently compressible elongated body 810, e.g., one is attached relatively posterior to the other. This allows the resiliently compressible elongated body 810 to lift at one end during flexion as shown in FIG. 8B and provide a counter force that stabilizes the spine.

Figure 9A:
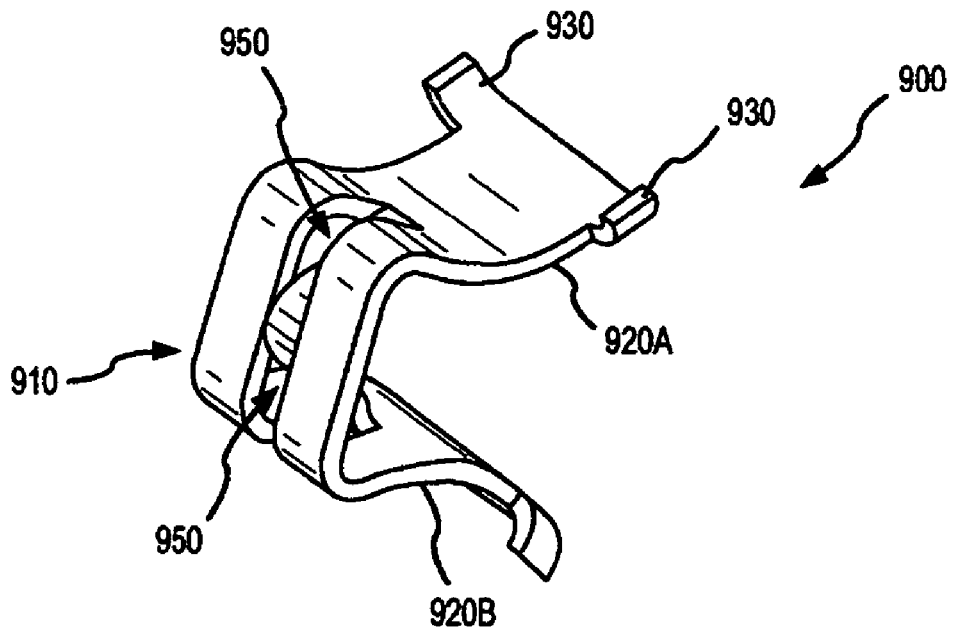
FIGS. 9A and 9B are two different perspective views of another embodiment of the interspinous stabilizer of the present invention.
Figure 9B:
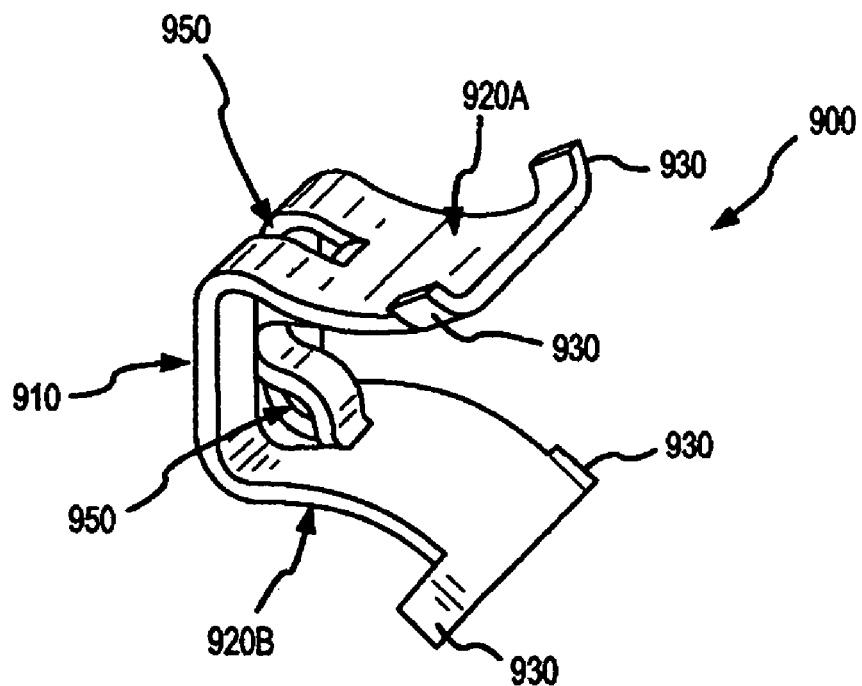
Figure 9C:
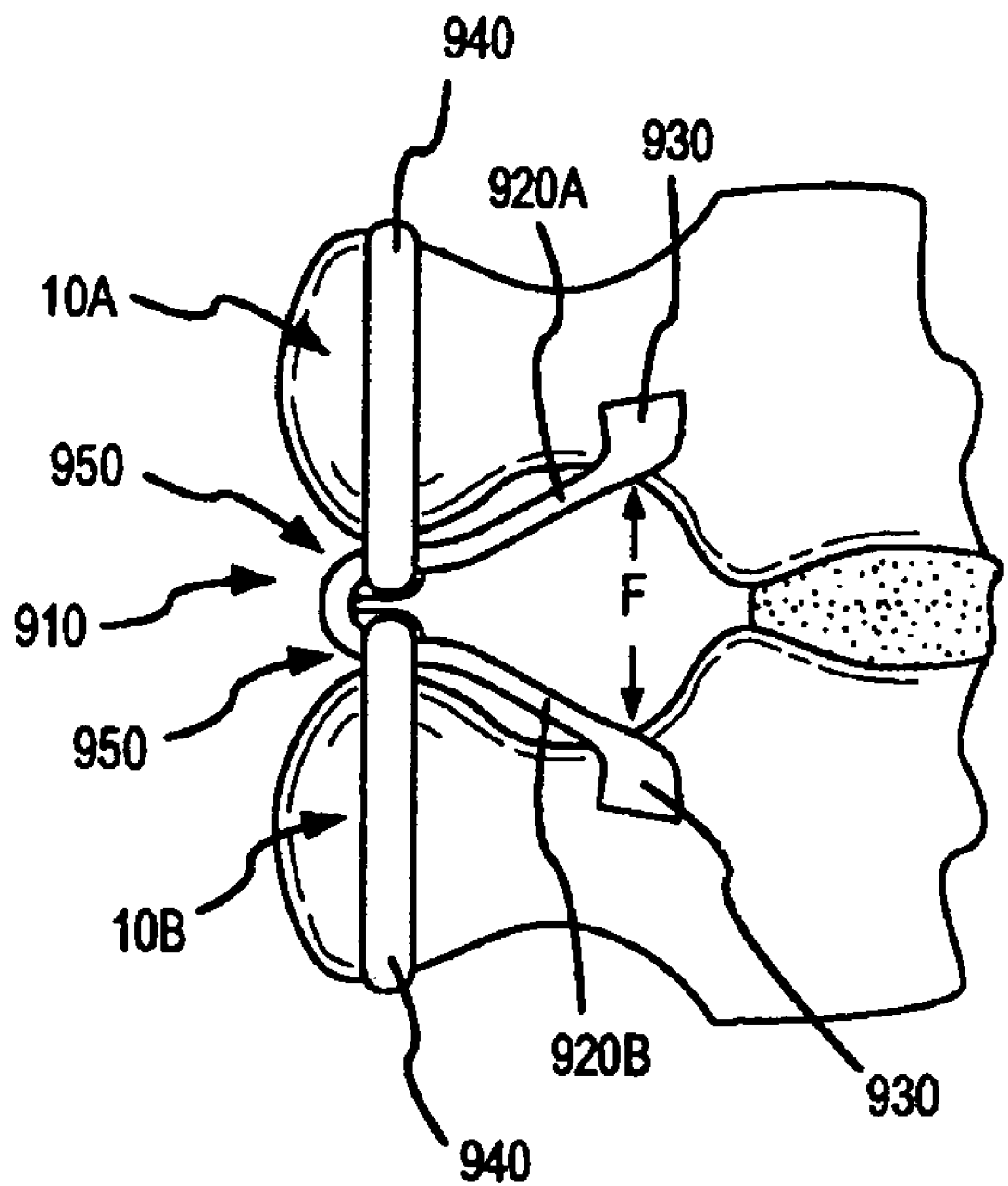
FIG. 9C is a side view of the interspinous stabilizer of FIGS. 9A and 9B following implantation.

FIGS. 9A, 9B, and 9C show another interspinous stabilizer 100 configuration of the present invention. This configuration comprises a resiliently flexible U-shaped body 900 comprising a central portion 910 and two branches 920A and 920B. The U-shaped body 900 is adapted for positioning between adjacent superior and inferior spinous processes (not shown in FIGS. 9A and 9B). Each of the branches 920A and 920B is adapted for contacting the surfaces of the spinous processes when the stabilizer 100 is implanted. The branches 920A and 920B can optionally comprise a pair of tabs 930 that project from an outer face of the branches, thereby providing a stirrup-like configuration for receiving a spinous process of a vertebra. These tabs 930 help stabilize and/or locate the U-shaped body 900 medial/laterally within the spinous processes.

The interspinous stabilizer 100 of FIGS. 9A, 9B, and 9C also comprises a resiliently stretchable anchoring member 940 that is operatively connected to near the central portion 910 of the U-shaped body 900. The anchoring member 940 is adapted for attaching to the superior and inferior spinous processes 10A and 10B.

The U-shaped body 900 may also comprise an anchoring member affixing element 950, preferably, within an interior surface of the U-shaped body 900. The anchoring member affixing element 950 is adapted to affix the optional anchoring member 940 to the U-shaped body 900. The anchoring member affixing element 950 can be an open slot located within the U-shaped body 900. In this manner, anchoring member 940 can be inserted through the open slot (i.e., anchoring member affixing element 950) and affixed to a spinous process. See FIG. 9B. While FIGS. 9A and 9B show a U-shaped body having two open slots for affixing the anchoring member 940, it should be appreciated that a single anchoring member affixing element 950 (e.g., an open slot) can be used to attach both anchoring members 940.

Generally, at the junction between the central portion 910 and the branches 920A and 920B, an opening is used as the anchoring member affixing element 950 to accommodate the method of attachment. The anchoring member affixing element 950 is typically used for affixing or placing a flexible cable, e.g., resiliently stretchable anchoring member 940, that maintains an appropriate mechanical advantage to support the vertebral bodies while reducing the incidence of kyphosis due to the moment induced as a result of the offset placement. The resiliently stretchable anchoring member can comprise, but is not limited to, a round cord or a flat strap.

The stabilizer 100 shown in FIG. 9A comprises a pair of relatively flat springs (branches 920A and 920B) that are relatively parallel to each other. However, as shown in FIG. 9C, these two flat springs need not be parallel to each other. In fact, in some cases it is preferred that these two springs are at an angle with respect to one another. Typical configuration will often be dictated by the configuration of the two adjacent spinous processes to be stabilized.

Preferably, the interspinous stabilizers 100 of the present invention provide rotational moment, i.e., apply force to restore lordosis, at all times. In some configurations, such as the interspinous stabilizers 100 illustrated in FIGS. 5, 6, 8A and 8B, can be made to apply rotational moment only in response to flexion induced kyphosis, i.e., forward bending of the spine by the patient.

Other aspects of the present invention provide methods for dynamically stabilizing vertebral bodies using various interspinous stabilizers 100 disclosed herein.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. An interspinous vertebral implant adapted for positioning between adjacent superior and inferior spinous processes, the interspinous vertebral implant comprising:
   a distraction member comprising a compressible body positionable between the superior and inferior spinous processes and adapted to apply opposing distraction forces on an anterior portion of the superior and inferior spinous processes; and
   an anchoring member including a spring encompassed within the distraction member and first and second arms extending from the spring, the first arm extending posteriorly from the spring to an end of the first arm and the second arm extending posteriorly from the spring to an end of the second arm, the end of the first arm configured to be attached to a posterior portion of the superior spinous process posterior of the anterior portion and the end of the second arm configured to be attached to a posterior portion of the inferior spinous process posterior of the anterior portion;
   wherein the spring is configured to draw the ends of the first and second arms toward one another to exert a compressive force on the posterior portions of the superior and inferior spinous processes while the distraction member applies opposing distraction forces on the anterior portions of the superior and inferior spinous processes.

2. The interspinous vertebral implant of claim 1, wherein the anchoring member is configured to create a rotational moment on the superior and inferior spinous processes with the distraction member being the center of the rotational moment.

3. The interspinous vertebral implant of claim 1, wherein the end of the first arm is a U-shaped end configured to hook over an edge of the superior spinous process.

4. The interspinous vertebral implant of claim 3, wherein the end of the second arm is a U-shaped end configured to hook over an edge of the superior spinous process.

5. The interspinous vertebral implant of claim 1, wherein the first arm is tapered such that the first arm has a width near the end of the first arm that is wider than a width of the first arm near the spring.

6. The interspinous vertebral implant of claim 5, wherein the second arm is tapered such that the second arm has a width near the end of the second arm that is wider than a width of the second arm near the spring.

* * * * *